United States Patent [19]

Solar

[11] Patent Number: 5,315,747
[45] Date of Patent: May 31, 1994

[54] METHOD OF PREPARING A BALLOON DILATATION CATHETER

[75] Inventor: Ronald J. Solar, San Diego, Calif.

[73] Assignee: Pameda N.V., Curacao, Netherlands Antilles

[21] Appl. No.: 969,946

[22] Filed: Oct. 30, 1992

[51] Int. Cl.⁵ ............................................. B23P 11/02
[52] U.S. Cl. ...................................... 29/447; 156/84; 128/DIG. 18; 264/573; 264/DIG. 71
[58] Field of Search ............................ 29/447; 285/381; 403/273; 156/85, 86, 84; 128/DIG. 18; 264/230, 573, DIG. 71

[56] References Cited

U.S. PATENT DOCUMENTS

| | | |
|---|---|---|
| 3,906,938 | 9/1975 | Fleischhacker . |
| 3,973,556 | 8/1976 | Fleischhacker . |
| 4,349,033 | 9/1982 | Eden . |
| 4,411,055 | 10/1983 | Simpson et al. ............... 29/447 |
| 4,467,790 | 8/1984 | Schiff . |
| 4,538,622 | 9/1985 | Samson et al. . |
| 4,545,390 | 10/1985 | Leary . |
| 4,554,929 | 11/1985 | Samson . |
| 4,601,713 | 7/1986 | Fuqua . |
| 4,619,274 | 10/1986 | Morrison . |
| 4,710,181 | 12/1987 | Fuqua . |
| 4,719,924 | 1/1988 | Crittenden et al. . |
| 4,734,093 | 3/1988 | Bonello et al. . |
| 4,738,666 | 4/1988 | Fuqua . |
| 4,757,827 | 7/1988 | Buchbinder et al. . |
| 4,762,129 | 8/1988 | Bonzel . |
| 4,784,639 | 11/1988 | Patel . |
| 4,787,899 | 11/1988 | Lazarus . |
| 4,793,350 | 12/1988 | Mar et al. . |
| 4,798,598 | 1/1989 | Bonello et al. . |
| 4,813,434 | 3/1989 | Buchbinder et al. . |
| 4,815,478 | 3/1989 | Buchbinder et al. . |
| 4,820,349 | 4/1989 | Saab . |
| 4,927,413 | 5/1990 | Hess . |
| 4,932,413 | 6/1990 | Shockey et al. . |
| 4,944,740 | 7/1990 | Buchbinder et al. . |
| 4,947,864 | 8/1990 | Shockey et al. . |
| 4,958,634 | 9/1990 | Jang . |
| 4,964,409 | 10/1990 | Tremulis . |
| 4,969,890 | 11/1990 | Sugita et al. . |
| 4,976,690 | 12/1990 | Solar et al. ...................... 604/96 |
| 5,040,548 | 8/1991 | Yock . |
| 5,041,089 | 8/1991 | Mueller et al. . |
| 5,049,131 | 9/1991 | Deuss . |
| 5,057,083 | 10/1991 | Gelllman . |
| 5,059,183 | 10/1991 | Semrod . |
| 5,059,186 | 10/1991 | Yamamato et al. . |
| 5,098,393 | 3/1992 | Amplatz et al. . |
| 5,104,399 | 4/1992 | Lazarus . |
| 5,106,368 | 4/1992 | Uldall et al. . |
| 5,116,309 | 5/1992 | Coll . |
| 5,135,535 | 8/1992 | Kramer . |
| 5,143,093 | 9/1992 | Sahota . |

*Primary Examiner*—Mark Rosenbaum
*Assistant Examiner*—David P. Bryant
*Attorney, Agent, or Firm*—Cowan, Liebowitz & Latman

[57] ABSTRACT

This invention relates to the preparation of a balloon dilatation catheter which comprises blowing a length of double lumen tubing to produce a double lumen catheter piece having distal and proximal ends and having a first lumen and a second lumen; cutting an opening in the second lumen proximal to the distal end of the catheter piece; inserting a pushing wire having distal and proximal ends into the second lumen through the proximal end of the catheter piece until the distal end of the pushing wire extends distally across the opening; inserting a piece of lubricous tubing into the second lumen through the distal end of the catheter piece; sealing the distal end of the first lumen; heating the distal portion of the catheter piece to cause the distal portion of the second lumen to shrink slightly to cause the lubricous tubing to fixedly engage the distal end of the pushing wire, while the first lumen is pressurized; and heating the remainder of the catheter piece to cause the second lumen to shrink around the pushing wire and the first lumen to shrink to define a balloon.

10 Claims, 2 Drawing Sheets

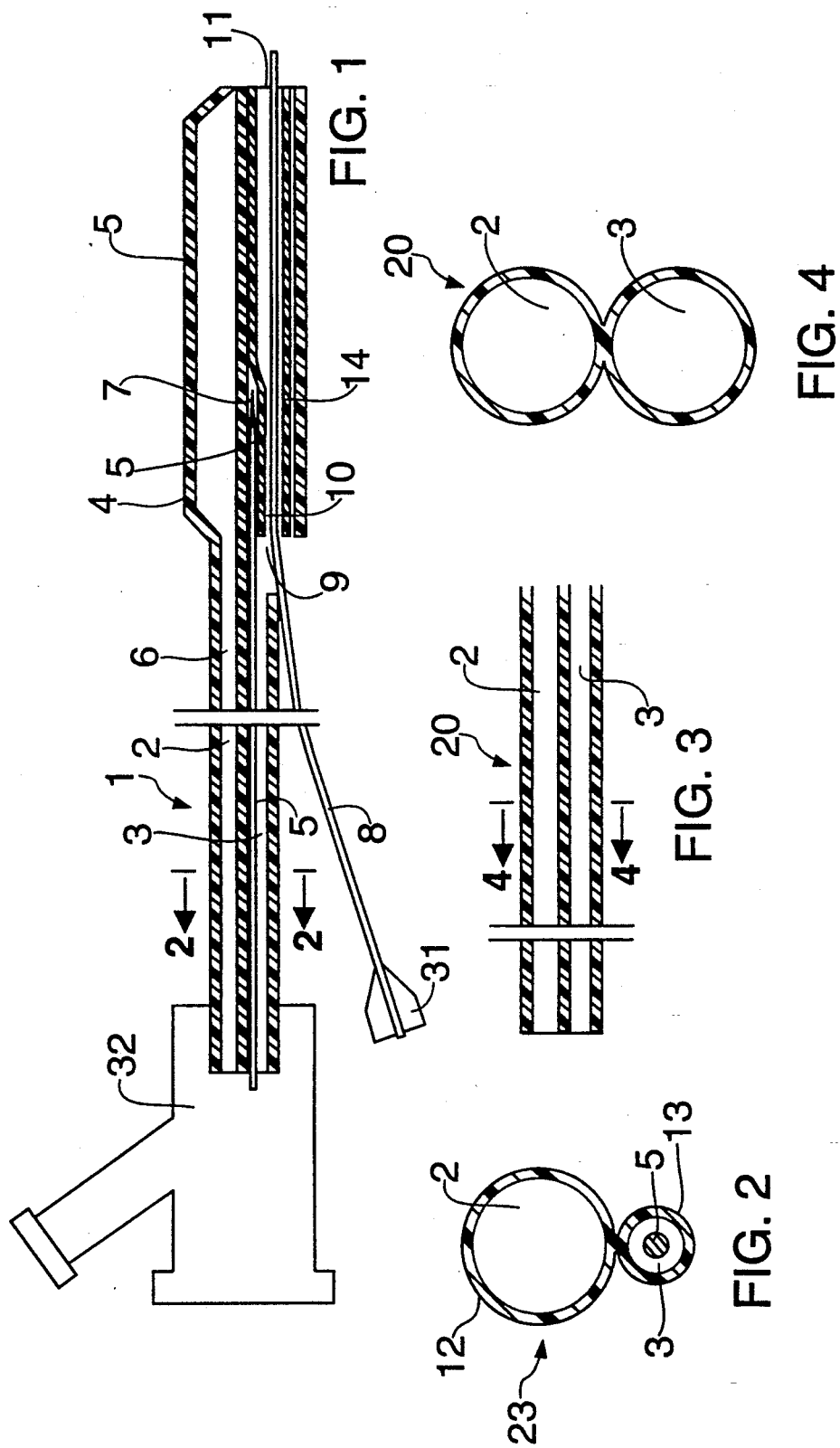

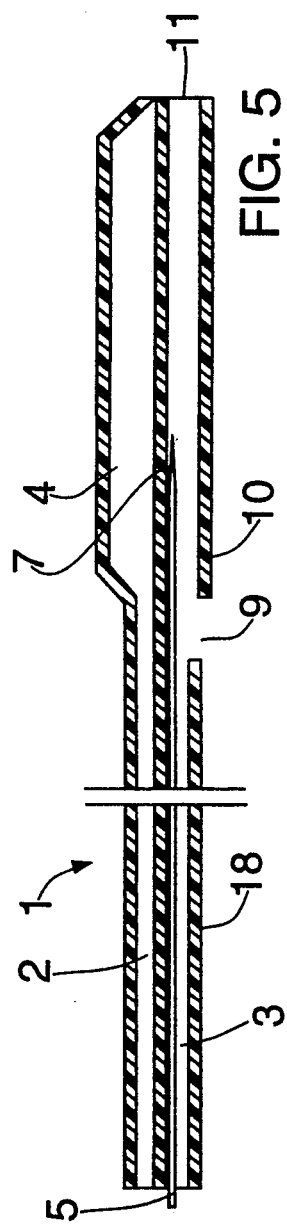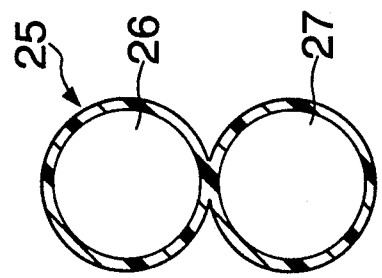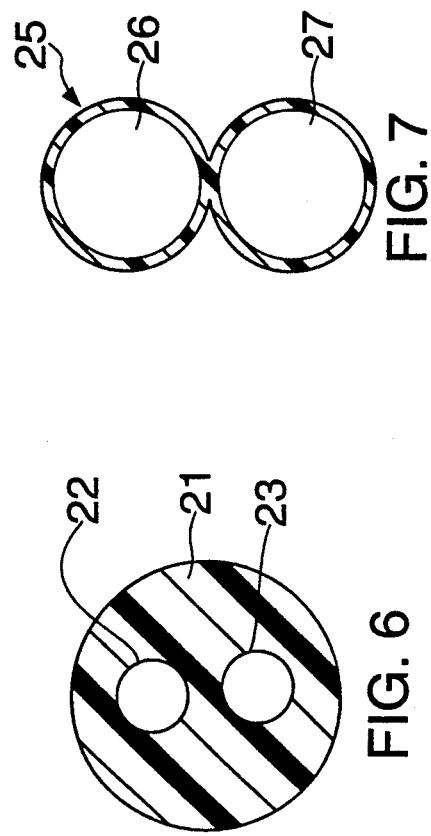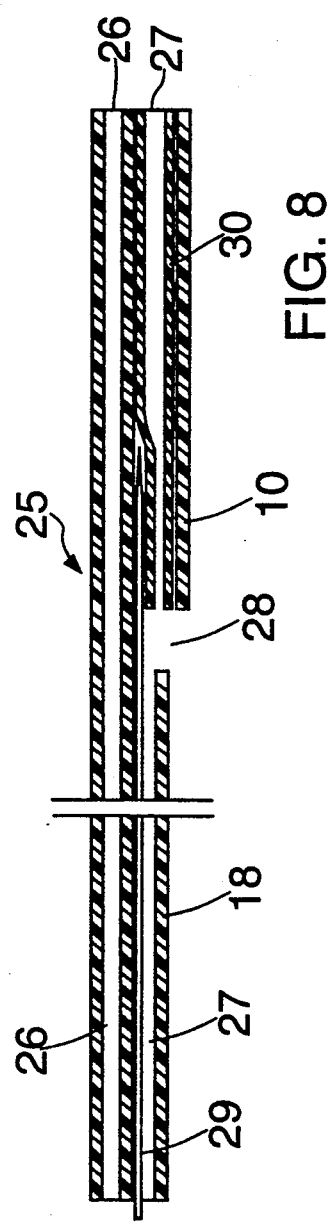

METHOD OF PREPARING A BALLOON DILATATION CATHETER

FIELD OF THE INVENTION

This invention is directed to the preparation of an angioplasty apparatus for facilitating rapid exchanges. More particularly, this invention is directed to the preparation of a rapid exchange catheter system whereby a double-lumen dilatation balloon catheter has an opening in one lumen adjacent its distal end for a guidewire and a pushing wire extending through the proximal portion of that same lumen.

BACKGROUND OF THE INVENTION

During angioplasty procedures it is often necessary to exchange one dilatation catheter for another. To do so requires manipulation of lengthy exchange wires, which is time consuming and awkward to the extent that two operators are required. A current approach to dealing with this is the "monorail" system wherein a dilatation catheter has a structure such that only the distal portion of the catheter tracks a guidewire. Examples of such systems are described in Yock, U.S. Pat. Nos. 5,040,548 and 5,061,273, Bonzel, U.S. Pat. No. 4,762,129, and Kramer, U.S. Pat. No. 5,135,535, all of which are incorporated herein by reference.

In the known monorail systems the pushing force on the dilatation catheter is eccentric to the guidewire, such that there is not total responsiveness in the system as the operator attempts to manipulate the dilatation catheter along the guidewire. This can cause binding and failure to move the catheter through tortuous arterial segments and tight stenoses. Furthermore, in these systems/designs, the guidewire lumen is positioned coaxially within a balloon that is attached to the catheter shaft at the proximal and distal ends of the balloon. This arrangement allows the balloon to compress along the guidewire lumen, increasing in profile, and thereby also causing binding and failure to move the catheter. Dependent upon the clinical application, balloons of varying lengths may be required. In addition to the time and expense required to develop and qualify separate balloons for each application, as the balloon length increases, the tendency for binding increases. Thus, there is a need for a monorail type system wherein there will be co-linear design between a push wire and the guidewire and a parallel arrangement between the balloon and the guidewire lumen, resulting in more positive tracking and facilitated passage through tortuous arterial segments and tight stenoses, as well as simplified methods of manufacture.

OBJECTS OF THE INVENTION

It is an object of the invention to provide a balloon dilatation system capable of rapid exchange.

It is also an object of the invention to provide a balloon dilatation system wherein a double lumen dilatation catheter has a pushing wire that extends through one lumen to a position adjacent or proximal to the dilatation balloon.

It is a further object of the invention to provide a double lumen dilatation catheter wherein the guidewire lumen is positioned exterior to the dilatation balloon.

It is yet a further object of the invention to provide a rapid exchange balloon dilatation catheter that is simple to manufacture.

These and other objects of the invention will become more apparent from the description below.

BRIEF DESCRIPTION OF THE DRAWINGS

FIG. 1 depicts a cross-sectional view of the distal portion of a balloon dilatation catheter according to the invention;

FIG. 2 represents a cross-sectional view along the line 2—2;

FIGS. 3, 5 and 7 represent perspective views of a distal portion of the catheter of the invention as it is being formed; and FIGS. 4, 6, and 8 represent cross-sectional views of workpieces from which the catheter of the invention can be formed.

DETAILED DESCRIPTION OF THE INVENTION

According to the invention, a balloon dilatation catheter comprises two substantially longitudinal coextensive lumens wherein the distal portion of one lumen terminates in a dilatation balloon. The other, second lumen is open at its distal end and is interrupted near its distal end to provide an opening for a guidewire that extends distally through the open distal end. Moreover, the second lumen comprises a pushing wire that extends from the proximal portion of the catheter to a point proximal, adjacent, or distal to the opening.

The invention can perhaps be better appreciated by making reference to the drawings. FIG. 1 depicts the distal portion of a balloon dilatation catheter 1 having coextensively extending lumens 2 and 3. Lumen 2 terminates in a dilatation balloon 4 which is inflated and deflated through lumen 2.

Lumen 3 contains pushing wire 5, which extends from the proximal end (not shown) of catheter 1 to a position 6 proximal or adjacent to balloon 4. The distal portion of pushing wire 5 is secured at position 6 by closure, e.g., heat-shrinking, of lumen 3 or by insertion of a plug or other holding means. Also, the distal portion 7 of pushing wire 5 is preferably tapered distally to provide a smooth transition in axial stiffness. The pushing wire 5 will become less stiff as the diameter of pushing wire 5 narrows in the distal direction. The tapering is substantially linear over the distal portion of the pushing wire 5. Such tapering can extend from about 2 to 40 cm from the distal end of the pushing wire 5. Optionally, instead of linear tapering, the tapering may be stepped, in discrete reductions, or otherwise nonlinear.

The distal portion of a guidewire 8 is threaded through opening 9 into the enlarged section, i.e., guidewire lumen, 10 of lumen 2. As the guidewire 8 is threaded into section 10, it exits through distal opening 11.

FIG. 2 represents a cross-sectional view showing how lumens 2 and 3 relate to one another and how pushing wire 5 is positioned within lumen 3. Lumen walls 12 and 13 can each have a thickness of from about 0.3 to 20 mil, preferably from about 0.5 to 10 mil. Lumen wall 13 will most likely be slightly thicker than lumen wall 12.

The lumen walls 12 and 13 are comprised of materials conventional to balloon dilatation catheters. Suitable materials include polyolefins such as polyethylene, polyethylene terepthalate, polyurethanes, polyesters, and various copolymers thereof. Pushing wire 5 can be made from any rigid, medically acceptable material suitable for such use, including, but not limited to wires or hypotubes comprised of stainless steel or other rigid materials.

The construction according to the invention leads to flexibility in product design. For example, the choice of pushing wire allows the designer to impart various features to the catheter in the form of various flexibility and pushability combinations. Also, a hollow pushing wire, or deletion or removal of the pushing wire, would facilitate infusion of fluids, drugs, and/or contrast media through the catheter into the distal vasculature. Further, it is within the scope of the invention that catheter 1 may have at least one additional, coextensive lumen that would similarly facilitate infusion of liquids, drugs and/or contrast media. For example, a catheter 1 with a third, coextensive lumen open at its distal end could have several possible applications.

In a preferred embodiment of the invention, as shown in FIG. 1, a lubricious coating or a section of thin tubing 14 of lubricious material is sealed into enlarged section 10. There are several known materials suitable for this purpose, such as polytetrafluoroethylene (available as TEFLON® from duPont), polyethylenes, polysiloxanes, etc. In this embodiment the tubing section 14 can hold the distal portion 7 of pushing wire 5 in position.

According to another embodiment of the invention a slitting means (31) is mounted proximally on guidewire 8. Then, as the catheter is withdrawn, the enlarged section 10 engages the slitter, the enlarged section 10 is slit, and catheter 1 is separated from guidewire 8. This would eliminate the requirement for the operator to change hands as catheter 1 is removed.

The catheter 1 may have visual length markings along its shaft that would enable the operator to predict when the catheter 1 would exit the guiding catheter into the vasculature. This would reduce the fluoroscopy time. The preferred design would put the markings directly on the pushing wire 5 (heat shrink tubing rings, inks, paints, etc.). Since the pushing wire 5 is encapsulated within the second lumen 3, the markings would not be exposed to the patient (i.e., markings would not come off, and materials which could be toxic if exposed may be used).

The preparation of a catheter 1 according to the invention is shown in FIGS. 3 to 8. After a double lumen workpiece 20 is prepared, the distal end of the workpiece is sealingly clamped, and heat and inflation pressure are applied to cause the distal portion of lumen 2 to expand to form the wall of balloon 4 and the distal portion of lumen 3 to expand to form enlarged section 10. The location where heat is applied can be varied to vary the respective lengths of balloon 4 and enlarged section 10. Heat sealing or application of suitable adhesive seals the distal portion of balloon 4. Opening 9 is cut into section 10, and opening 11 is maintained or created by trimming the distal portion of the catheter 1. Pushing wire 5 is then inserted into lumen 3, wherein either the remaining proximal portion 18, or more, of lumen 3 is heat shrunk to cause pushing wire 5 to be positively engaged by lumen 3. Alternatively, the distal portion of pushing wire 5 could be affixed by suitable means, such as an adhesive or a plug, in lumen 3.

Workpiece 20 can be prepared by methods well-known to those skilled in the art. In a preferred method workpiece 20 can be prepared by blowing extruded tubing 21, a cross-section of which is shown in FIG. 6.

In a preferred embodiment of the invention, catheter 1 can be prepared from extruded tubing 21 by blowing said tubing 21 under pressure and heating conditions sufficient to produce a catheter piece 25, a cross-section of which is shown in FIG. 7, where the diameters of lumens 26 and 27 correspond substantially to the final diameters of balloon 4 and enlarged section 10, respectively. The holes or openings 22 and 23 in tubing 21 are not necessarily the same, such that the diameters of lumens 26 and 27 may also differ.

After an opening 28 (corresponding to opening 9) is cut into lumen 27 at a point to define the length of the guidewire lumen or enlarged section 10, a pushing wire 29 is inserted into lumen 27. Pushing wire 29 extends the length of lumen 27 to a point slightly distal of opening 28. Preferably a lubricious liner 30 is inserted into the distal end of lumen 27. Then, the distal end of lumen 26 is sealed, and, while lumen 26 is pressurized, heat is applied to the distal portion of catheter piece 25 to cause lumen 27 to slightly shrink around liner 30, which fixedly engages the distal end of pushing wire 29. Next, the portion of catheter piece 25 proximal to the balloon is heated to shrink lumen 26 and to shrink lumen 27 around pushing wire 29. The balloon length is determined by the location where heat is applied to lumen 26.

When portions of the catheter are heated, the heating can be effected by a point source of heat, where the point source is moved along the exterior of the catheter or the catheter is moved across the point source. Alternatively, the heat can be applied with a broader heat source, such as a hot water bath. The source of and/or techniques of heating will be apparent to those skilled in the art.

Also, in a preferred embodiment of the invention the workpiece will optionally be cross-linked prior to working. Such cross-linking could be effected by chemical or irradiation means. The workpiece can be optionally or additionally oriented by mechanical means, such as stretching during blowing.

The catheters of the invention are prepared by use of techniques and procedures known to those skilled in the art. For example, the pressure and heating conditions will vary according to the materials used and the results desired, and it is well within the skill of those skilled in the art to determine the proper pressure and heating requirements.

An additional advantage of the design and preparation according to the invention is that the catheter can be of integral design and multiple bonding steps can be avoided. The balloon and both lumens can be formed from a single piece. This design permits improvements in manufacturing yields, quality, and reliability due to simplified construction.

Guidewire 8 may be a conventional guidewire, preferably a spring guidewire, as is well known. Typical guidewires are shown in U.S. Pat. Nos. 4,757,827, 4,815,478, 4,813,434, 4,619,274, 4,554,929, 4,545,390, 4,538,622, 3,906,938, 3,973,556, and 4,719,924, all of which are incorporated herein by reference. In addition, the shaft of guidewire 8 could be solid or hollow, such as a hypotube, with an open distal end, to facilitate drug infusion.

Operation and use of the angioplasty apparatus shown in FIG. 1 may now be briefly described as follows: A guiding catheter is inserted into the coronary artery in a conventional manner. The guidewire 8 is then introduced into the guiding catheter and advanced to and across the lesion. Now, the balloon dilatation catheter is inserted onto the guidewire by a back loading technique, where the proximal extremity of the guidewire 8 is inserted backwardly through the tip 11 of the balloon dilatation catheter 1 through the enlarged section 10, and exits opening 9. The catheter 1 is then advanced along the guidewire 8 to and across the lesion.

After the balloon 4 has crossed the stenosis or lesion, the balloon 4 can be inflated in a conventional manner by introducing a radiopaque contrast liquid through the lumen 2. After the inflation has occurred and the desired operation has been performed by enlarging the opening in the stenosis, the balloon dilatation catheter 1 can be removed very rapidly by holding the guidewire 8 stationary and withdrawing the balloon dilatation catheter.

If it is ascertained by the operator that additional dilatation of the stenosis is desired and that a larger balloon should be inserted into the stenosis, this can be accomplished very rapidly by selecting the desired size of balloon dilation catheter and repeating the aforementioned procedure. The balloon of the new dilatation catheter can be inflated in the same manner as hereinbefore described. If necessary, even another exchange procedure can be readily accomplished in the same manner as hereinbefore described utilizing a still larger balloon dilatation catheter if that turns out to be necessary.

After the desired amount of dilation of the stenosis or lesion has been accomplished, the balloon dilatation catheter can be removed and thereafter the guiding catheter can be removed.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A method of preparing a balloon dilatation catheter which comprises the steps of:
   (a) blowing a length of multiple lumen tubing to produce a double lumen catheter piece having distal and proximal ends and having a first lumen and a second lumen;
   (b) cutting an opening in the second lumen proximal to the distal end of the catheter piece;
   (c) inserting a pushing wire having distal and proximal ends into the second lumen through the proximal end of the catheter piece until the distal end of the pushing wire extends distally across the opening;
   (d) inserting a piece of lubricious tubing having proximal and distal ends proximally into the second lumen through the distal end of the catheter piece so that the proximal end of the lubricious tubing overlaps the distal end of the pushing wire;
   (e) sealing the distal end of the first lumen;
   (f) heating the distal portion of the catheter piece to cause the distal portion of the second lumen to shrink slightly to cause the lubricious tubing to fixedly engage the distal end of the pushing wire, while the first lumen is pressurized to prevent shrinkage of the distal portion thereof; and
   (g) heating the remaining portion of the catheter piece to cause the second lumen to shrink around the pushing wire and the first lumen to shrink to define a balloon at the distal end thereof.

2. The method of claim 1, which comprises the additional step of attaching a fluid communication means to the proximal end of the catheter piece to enable the first lumen to be in fluid communication with an inflation fluid source.

3. The method of claim 1, wherein the tubing blown in step (a) has more than two lumens.

4. The method of claim 3, wherein the tubing has at least one lumen having an open distal end.

5. The method of claim 4, which comprises the additional step of attaching fluid communication means to the proximal end of the catheter to enable the first lumen to be in fluid communication with an inflation fluid source and to enable at least one additional lumen to be in fluid communication with the proximal end of the catheter.

6. A method of preparing a balloon dilatation catheter which comprises the steps of:
   (a) blowing a length of multiple lumen tubing to produce a double lumen catheter having distal and proximal ends and having first and second lumens having respective proximal and distal ends;
   (b) sealing the distal end of the first lumen;
   (c) inflating the first lumen to cause a dilatation balloon to form in the first lumen proximal to the distal end of the first lumen;
   (d) cutting an opening in the second lumen proximal to the distal end of the catheter;
   (e) inserting a pushing wire having distal and proximal ends into the second lumen through the proximal end of the catheter until the distal end of the pushing wire extends distally across the opening;
   (f) inserting a piece of lubricious tubing having proximal and distal ends proximally into the second lumen through the distal end of the catheter so that the proximal end of the lubricious tubing overlaps the distal end of the pushing wire;
   (g) heating the distal portion of the catheter to cause the distal portion of the second lumen to shrink slightly to cause the lubricous tubing to fixedly engage the distal end of the pushing wire, while the first lumen is pressurized to prevent shrinkage of the preformed dilatation balloon; and
   (h) heating the remaining portion of the catheter to cause the second lumen to shrink around the pushing wire.

7. The method of claim 6, which comprises the additional step of attaching a fluid communication means to the proximal end of the catheter to enable the first lumen to be in fluid communication with an inflation fluid source.

8. The method of claim 6, wherein the tubing blown in step (a) has more than two lumens.

9. The method of claim 8, wherein the tubing has at least one lumen having an open distal end.

10. The method of claim 9, which comprises the additional step of attaching fluid communication means to the proximal end of the catheter to enable the first lumen to be in fluid communication with an inflation fluid source and to enable at least one additional lumen to be in fluid communication with the proximal end of the catheter.

* * * * *